United States Patent
Sandrock et al.

(10) Patent No.: US 10,351,823 B2
(45) Date of Patent: Jul. 16, 2019

(54) METHODS AND COMPOSITIONS FOR EXPANDING, IDENTIFYING, CHARACTERIZING AND ENHANCING POTENCY OF MAMMALIAN-DERIVED GLIAL RESTRICTED PROGENITOR CELLS

(75) Inventors: Robert Sandrock, San Carlos, CA (US); James T. Campanelli, Holladay, UT (US); Deborah A. Eppstein, Salt Lake City, UT (US)

(73) Assignee: Q THERAPEUTICS, INC., Salt Lake City, UT (US)

( * ) Notice: Subject to any disclaimer, the term of this patent is extended or adjusted under 35 U.S.C. 154(b) by 0 days.

(21) Appl. No.: 13/508,803

(22) PCT Filed: Nov. 9, 2010

(86) PCT No.: PCT/US2010/055956
§ 371 (c)(1),
(2), (4) Date: May 9, 2012

(87) PCT Pub. No.: WO2011/059952
PCT Pub. Date: May 19, 2011

(65) Prior Publication Data
US 2012/0230963 A1    Sep. 13, 2012

Related U.S. Application Data

(60) Provisional application No. 61/260,441, filed on Nov. 12, 2009, provisional application No. 61/326,799, filed on Apr. 22, 2010.

(51) Int. Cl.
*C12N 5/079*  (2010.01)

(52) U.S. Cl.
CPC .................. *C12N 5/0622* (2013.01)

(58) Field of Classification Search
CPC ... C12N 5/0622; A61K 35/12; G01N 33/5058
USPC ......................................................... 424/93.7
See application file for complete search history.

(56) References Cited

U.S. PATENT DOCUMENTS

| 2007/0037222 A1* | 2/2007 | Rao et al. ...................... 435/7.2 |
| 2008/0138895 A1 | 6/2008 | Wahlberg et al. ............ 435/352 |

FOREIGN PATENT DOCUMENTS

| EP | 10830580.6 | 8/2013 |
| WO | WO 2009/023795 A2 | 2/2009 |

OTHER PUBLICATIONS

Mujtaba et al., Isolation of Lineage-Restricted Neural Precursors from Cultured ES Cells, Chapter 16, From: Methods in Molecular Biology, vol. 185: Embryonic Stem Cells: Methods and Protocols, Edited by: K. Turksen, Humana Press Inc., Totowa, NJ, pp. 189-204 (2002).*

(Continued)

*Primary Examiner* — Jennifer M. H. Tichy
(74) *Attorney, Agent, or Firm* — Licata & Tyrrell P.C.

(57) ABSTRACT

Methods for producing a population of human-derived glial restricted progenitor cells (GRPs) with decreased potentially unintended or undesired cellular phenotypes and/or decreased standard deviation in the cells of the population are provided. Also provided are antibody panels and gene expression profiles to characterize GRPs and a method for its use in characterizing GRP cells. In addition methods for use of these GRP cells to generate astrocytes and/or oligodendrocytes, to re-myelinate neurons and to treat glial cell related and other neurodegenerative diseases or disorders or injuries or damage to the nervous system are provided. A method to manufacture neural cells depleted of A2B5 positive cells is also provided.

32 Claims, 3 Drawing Sheets

(56) References Cited

OTHER PUBLICATIONS

Dietrich et al. "Characterization of A2B5+ Glial Precursor Cells from Cryopreserved Human Fetal Brain Progenitor Cells" Glia 2002 40(1):65-77.
Hardison et al. "Transplantation of Glial-committed Progenitor Cells into a Viral Model of Multiple Sclerosis Induces Remyelination in the Absence of an Attenuated Inflammatory Response" Experimental Neurology 2006 197(2):420-429.
Lassmann et al. "Remyelination in Multiple Sclerosis" Multiple Sclerosis 1997 3(2):133-136.
Prineas et al. "Multiple Sclerosis: Remyelination of Nascent Lesions" Annals of Neurology 1997 33(2):137-151.
Prineas, J. W. and Connell, F. "Remyelination in multiple sclerosis" Annals of Neurology 1979 5(1):22-31.
Rao, M. S. and Mayer-Proschel, M. "Glial-restricted Precursors Are Derived from Multipotent Neuroepithelial Stem Cells" Developmental Biology 1997 188:48-63.
Saito et al. "The Specificity of Monoclonal Antibody A2B5 to C-series Gangliosides" Journal of Neurochemistry 2001 78:64-74.
Totoiu et al. "Remyelination, Axonal Sparing, and Locomotor Recovery Following Transplantation of Glial-committed Progenitor Cells into the MHV Model of Multiple Sclerosis" Experimental Neurology 2004 187(2):254-265.
Windrem et al. "Fetal and Adult Human Oligodendrocyte Progenitor Cell Isolates Myelinate the Congenitally Dysmyelinated Brain" Nature Medicine 2004 10(1):93-97.
Windrem et al. "Neonatal Chimerization with Human Glial Progenitor Cells Can Both Remyelinate and Rescue the Otherwise Lethally Hypomyelinated Shiverer Mouse" Cell Stem Cell 2008 2:553-565.
Campanelli et al. "Expression Profiling of Human Glial Precursors" BMC Developmental Biology 2008 8:102.
Sandrock et al. "Isolation, Characterization and Preclinical Development of Human Glial-Restricted Progenitor Cells for Treatment of Neurological Disorders" Regenerative Medicine 2010 5(3):381-394.
Rao et al. "A Tripotential Glial Precursor Cell is Present in the Developing Spinal Cord" Proc. Natl. Acad. Sci. USA 1998 95:3996-4001.

* cited by examiner

METHODS AND COMPOSITIONS FOR EXPANDING, IDENTIFYING, CHARACTERIZING AND ENHANCING POTENCY OF MAMMALIAN-DERIVED GLIAL RESTRICTED PROGENITOR CELLS

This patent application is the U.S. National Stage of PCT Application No. PCT/2010/055956, filed Nov. 9, 2010, which claims the benefit of priority from U.S. Provisional Application Ser. No. 61/326,799, filed Apr. 22, 2010 and U.S. Provisional Application Ser. No. 61/260,441, filed Nov. 12, 2009, teachings of each of which are herein incorporated by reference in their entireties.

FIELD OF THE INVENTION

The present invention provides manufacturing methods for a population of mammalian-derived glial restricted progenitor cells (GRPs) with decreased potentially unintended cellular phenotypes and/or decreased standard deviation in the cells of the population as well as methods for use of these cells. Also provided in the present invention is an antibody panel to characterize GRPs and a method for its use in characterizing GRP cells.

BACKGROUND OF THE INVENTION

Glial restricted progenitor cells (GRPs) are defined by their reactivity with antibody A2B5, which recognizes a subset of c-series gangliosides (Dietrich et al., Glia 2002 40:65-77; Rao and Mayer-Proschel, Dev. Biol. 1997 188:48-63; Saito et al., J. Neurochem. 2001 78:64-74; Windrem et al., Nat. Med. 2004 10:93-97). Other antigenic characteristics of GRPs include moderate expression of the astrocytic marker glial fibrillary acidic protein (GFAP) and low expression of the neuronal markers E-CAM (polysialated N-CAM, or PSA-NCAM) and β-III tubulin (TuJ1) Dietrich et al., Glia 2002 40:65-77; Rao and Mayer-Proschel, Dev. Biol. 1997 188:48-63).

At the time the GRPs are isolated they have already differentiated endogenously beyond neural stem cells into committed lineage-restricted cells. GRPs have not been observed to induce or produce teratomas.

A very important category of neuron in the brain and spinal cord comprises those whose axons are ensheathed in myelin. When this myelin sheath is damaged, oligodendrocytes, whose living processes constitute the insulating myelin layer around neuronal axons, are destroyed. Demyelinated neurons cannot properly conduct signals and eventually will die.

When damage is incomplete, endogenous repair mechanisms are activated resulting in remyelination and partial or full return of function (Lassmann et al., Mult. Scler. 1997 3:133-136; Prineas and Connell, Ann. Neurol. 1979 5:22-31). This demonstrates the critical point that remyelination can indeed lead to restoration of function. However, the majority of patients who experience demyelination due to various diseases or trauma do not experience sufficient endogenous remyelination (Prineas et al., Ann. Neurol. 1993 33:137-151), and despite much need and effort, little progress has been made in developing products that can help restore lost function. This can be partially attributed to the multiple signals and intricate intercellular interactions that must occur to effect regeneration of the damaged myelin-producing oligodendrocytes in vivo. It is significant that cellular therapy resulting in remyelination has been demonstrated to be beneficial in animal models of demyelination.

Totoiu et al. (Exp. Neurol. 2004 187:254-265) reported benefits of local implants of murine GRPs in treating spinal cord lesions in a viral-induced murine MS model. The GRPs migrated and differentiated into oligodendrocytes, resulting in remyelination that appeared to be associated with axonal sparing. They also observed improved locomotion. Subsequent studies (Hardison et al. Exp. Neurol. 2006 197:420-429) demonstrated that the murine GRPs were able to survive and remyelinate in the presence of both inflammatory T cells and macrophages.

The shiverer mouse, which exhibits defects in production of normal myelin due to a mutation in the gene encoding myelin basic protein, is a model to study the effect of exogenous cell transplants on myelin production. Demonstration of myelin production by cellular transplants into shiverer is relevant for many demyelinating diseases, including TM and MS, as well as those of dysmyelination. Human GRPs have been shown to be capable of widespread and high-efficiency myelination of the shiverer mouse brain after perinatal xenograft (Windrem et al., Nat. Med. 2004 10:93-97). Differentiation into regionally appropriate cell types (astrocytes and oligodendrocytes) was demonstrated with no evidence of tumors. These studies were extended to show remyelination of both brain and spinal cord, which is accompanied by substantial phenotypic rescue in a subset of the implanted animals (Windrem et al., Cell Stem Cell 2008 2:553-565).

SUMMARY OF THE INVENTION

An aspect of the present invention relates to methods for manufacturing mammalian glial restricted progenitor (GRP) cells.

Another aspect of the present invention relates to a method for decreasing unintended cellular phenotypes in a GRP cell population and/or decreasing standard deviations in cells of the GRP cell population.

Another aspect of the present invention relates to an antibody panel for characterizing GRP cells comprising antibodies to c-series gangliosides (using A2B5 antibody), GFAP, and one or more antibodies selected from the group consisting of Olig1, Olig2, O1, PDGFR-β, nestin, NG2, PSA-NCAM, TuJ1, Ki-67 and NeuN, and methods for characterizing cells as GRP cells with this panel of antibodies.

Another aspect of the present invention relates to gene expression profiles useful in characterizing GRP cells.

Another aspect of the present invention relates to a method for manufacturing mammalian neural cells depleted of A2B5-positive cells.

Another aspect of the present invention relates to methods for use of these manufactured mammalian GRP cells to generate astrocytes and/or oligodendrocytes.

Another aspect of the present invention relates to methods for use of these manufactured mammalian GRP cells to increasing re-myelination of neurons in a mammal suffering from a disease, disorder, injury or damage associated with demyelination of neurons.

Another aspect of the present invention relates to methods for use of these manufactured mammalian GRP cells to reducing glial scar formation.

Yet another aspect of the present invention relates to methods for use of these manufactured mammalian GRP cells in the treatment of neurodegenerative diseases or disorders or damage or injury to the nervous system or a portion thereof in mammals.

DETAILED DESCRIPTION OF THE INVENTION

Figure 1:
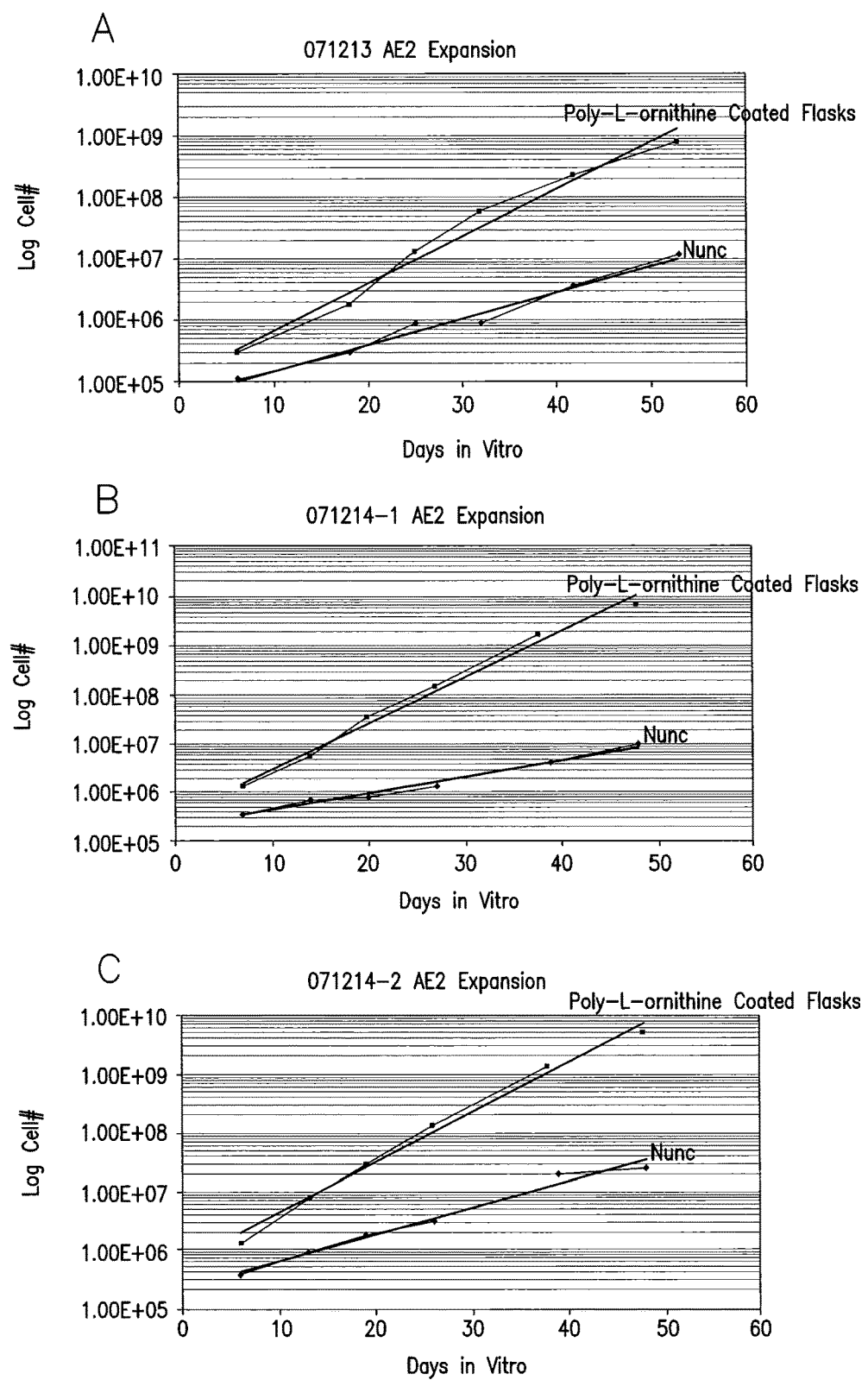
FIGS. 1A, 1B and 1C show pilot scale growth curves of three independent cell preparations manufactured in accordance with the present invention.

The present invention provides methods for manufacturing mammalian glial progenitor cells (GRPs). GRPs are also referred to as glial restricted precursor cells or glial progenitor cells in the literature.

Mammalian GRP cells of the present invention can be derived from any mammalian tissue source capable of generating A2B5 positive cells. Examples of such mammalian tissue sources include, without limitation, embryonic/fetal, and adult (inclusive of all ages after birth) sources, all from tissues including, but not limited to neural, brain, spinal cord, optic nerve, olfactory epithelium, endocrine, skin, muscle, fat, connective, placental, cord blood, blood, bone marrow, bone, embryonic stem cells, and induced pluripotent cells. By capable of generating A2B5 positive cells it is meant to include mammalian tissue sources differentiated into A2B5 positive cells, mammalian tissue sources de-differentiated into A2B5 positive cells, as well as mammalian tissue sources de-differentiated and then differentiated into A2B5 positive cells.

Mammalian glial restricted progenitor (GRP) cells are manufactured in accordance with the present invention by isolating A2B5 antibody-reactive cells from a mammalian tissue source capable of generating A2B5 positive cells. The A2B5-positive cells are then cultured for greater than 6 days in vitro (DIV) on a substrate. The cultured cells are then harvested.

In one embodiment of the present invention, the method comprises dissociating mammalian neural tissue such as, but not limited to, fetal cadaver forebrain tissue, fetal cadaver spinal cord tissue, mammalian biopsy brain or spinal cord tissue, or the like into a cell suspension. In one embodiment, the mammalian neural tissue is obtained after neural tube closure. For human GRPs, neural tissue obtained after neural tube closure, at, for example about 14 to about 24 gestational week tissues as been demonstrated to yield consistent product. Dissociation is performed either enzymatically, mechanically, or both enzymatically and mechanically in accordance with known methods.

A2B5 antibody-reactive cells can be isolated be various means known to those of skill in the art. For example, in one embodiment, the A2B5 antibody-reactive cells are isolated using magnetic activated cell sorting. For example, cells can be passed over a column after a single A2B5 antibody labeling using Miltenyi magnetic bead technology or Dynal Magnetic bead technology or other known suitable antibody separation technologies. Alternatively, antibody positive cells can be captured using fluorescence activated cell sorting or immunopanning via standard methods. The column (or FACS or immunopanning dishes) enriches for A2B5(+) cells and reduces A2B5(−) cells. Passage over an additional column or columns (or an additional FACS or immunopanning dish or dishes) effectively reduces intermediately positive cells and enriches for highly positive cells.

The A2B5-positive population is then cultured for greater than 6 days in vitro (DIV), for example approximately 10-20-DIV, 15-20 DIV, at least 20 DIV and/or up to 100 DIV or greater, or at least two passages and the cultured cells are harvested and frozen.

This manufacturing process differs from previously described manufacturing processes in that a method of sorting desired cells with a single antibody is used and the growth is extended from 6-DIV with no passaging to growth for up to two passages or greater than 6-DIV, for example approximately 10-20-DIV, 15-20 DIV, at least 20 DIV, or up to 100 DIV or greater. Further, cells are grown not in suspension but rather on a substrate for adherence of cells.

Examples of substrates include, but are not limited to, poly-L-ornithine, poly-L-lysine and recombinant or natural extracellular matrix molecules or fragments thereof, such as, but not limited to laminin, fibronectin and CELLstart™ (xeno-free substrate for attachment and expansion of human embryonic, mesenchymal, and neural stem cells, Invitrogen Corporation, Carlsbad, Calif.).

Growth curves, yields, and immunologically defined phenotypes of cells manufactured in accordance with the method of the present invention exhibit tightened variability and decreased unintended cellular phenotypes without altering their therapeutic ability.

Phase contrast microscopy revealed a stable morphological phenotype prior to the first passage (6-DIV) at the end of the second passage (20-DIV; harvest) and up to 100 days in vitro. This bi- to multi-polar morphology is consistent across preparations with three independent cell preparations.

Pilot scale growth curves of cells manufactured in accordance with the present invention are depicted in FIG. 1A through 1C. Three independent cell preparations are shown in FIGS. 1A, 1B and 1C, respectively, as is a comparison of growth on untreated plastic ("suspension") and growth on poly-L-ornithine treated tissue culture plastic. Cell preparations grown on substrate-coated flasks exhibited increased slope and increased plating efficiency.

Figure 2:
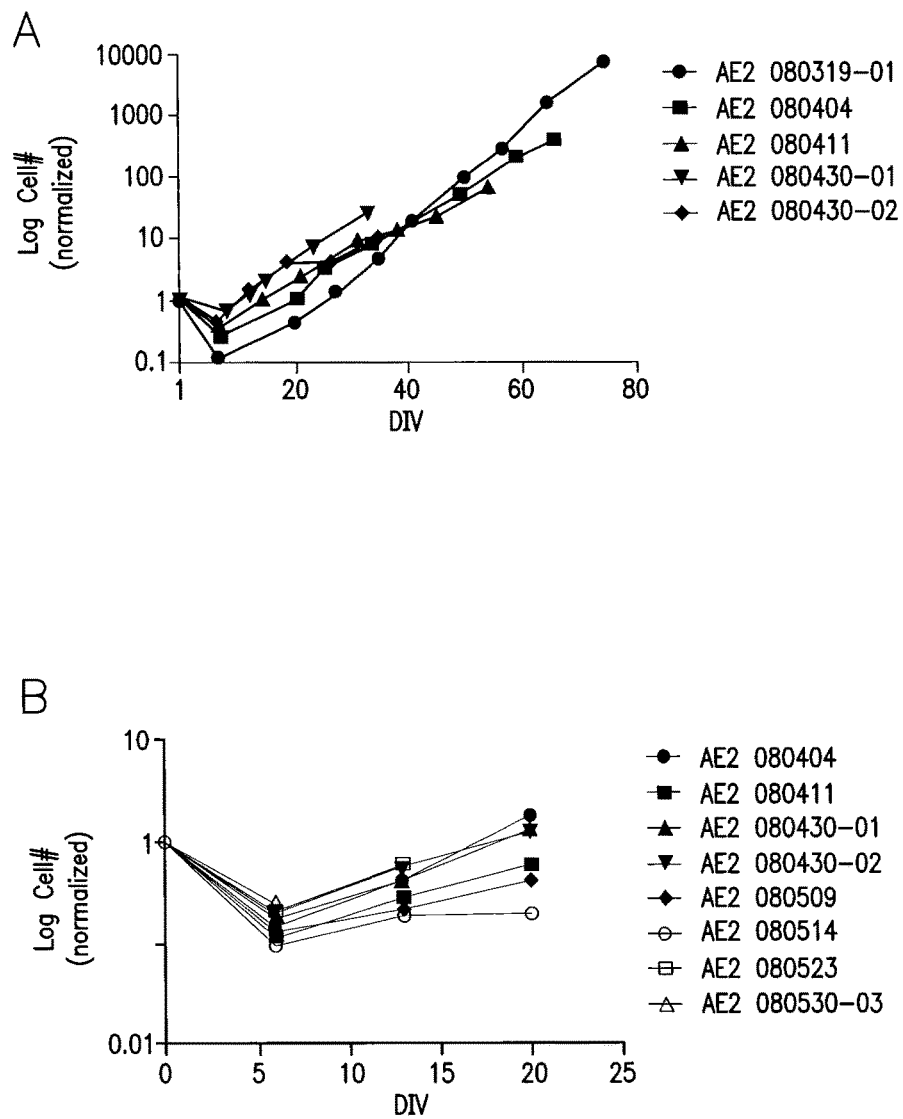
FIGS. 2A and 2B show production-scale growth curves of cells manufactured in accordance with the present invention.

Production-scale growth curves are depicted in FIGS. 2A and 2B. These curves are similar to the pilot scale and demonstrate the cells harvested at 20-DIV are not nearing senescence.

Figure 3:
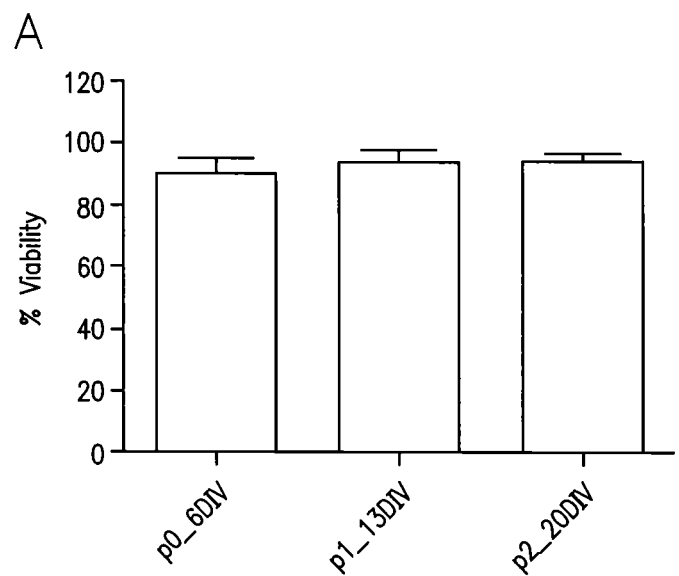
FIGS. 3A and 3B show a comparison of cell viability on suspension versus poly-L-ornithine treated surfaces (FIG. 3B) as well as the viability at each passage and final harvest (FIG. 3A).
Figure 3:
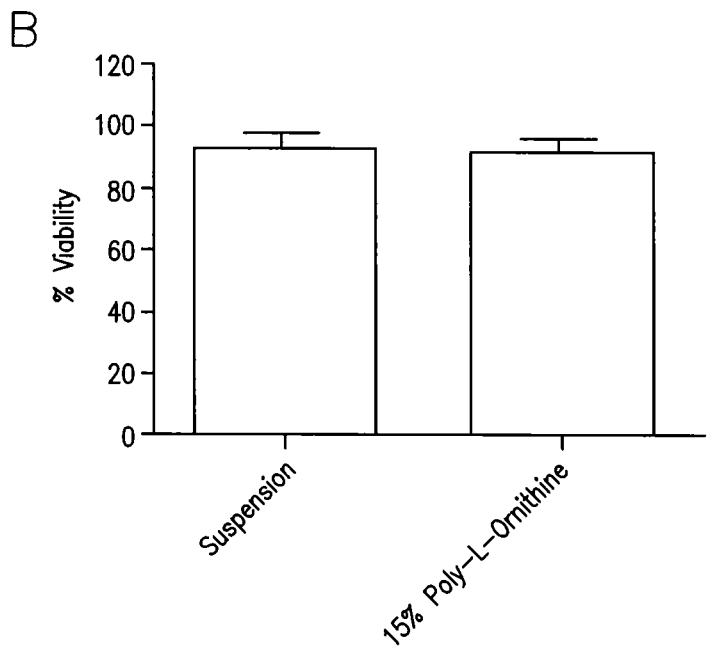

Cell viability was assessed by the trypan blue exclusion method. Comparison of viability on suspension versus poly-L-ornithine treated surfaces is shown in FIG. 3B, while the viability at each passage and final harvest is shown in FIG. 3A. In all cases mean viability values exceed 90%.

Cells manufactured in accordance with the present invention were immunophenotyped using a panel of antibodies which recognize desired phenotypes (glial restricted progenitors and their progeny) as well as potential contaminating unintended cellular phenotypes (neuronal progenitors, neurons, microglia and endothelial cells). Antibodies in this panel are chosen from A2B5, GFAP, PDGFR-α, Olig1, Olig2, O1, nestin, NG2, PSA-NCAM, Tun, Ki-67 and/or NeuN. Immunophenotyping with this unique panel of antibodies showed a decrease in potentially unintended cellular phenotypes (PSA-NCAM and TuJ1) at greater than 6-DIV versus 6-DIV, as well as a decrease in the standard deviations in cells produced in accordance with the method of the present invention.

Accordingly, another aspect of the present invention relates to a method for decreasing potentially unintended cellular phenotypes in a GRP cell population and/or decreasing standard deviations in cells of the GRP cell population which comprises harvesting cells for greater than 6-DIV. The decrease in potentially unintended cellular phenotypes and/or decrease in standard deviations in cells is determined by comparison to cells harvested at 6-DIV.

It has also been found that freezing and thawing of a GRP cell population further decreases unintended phenotype. While the desirable A2B5, GFAP and Ki-67 positive phenotypes are retained upon freeze/thaw, the markers for unintended cellular phenotypes (PSA-NCAM and TuJ1) are reduced by >50%.

Accordingly, another aspect of the present invention relates to a method for decreasing potentially unintended cellular phenotypes in a GRP cell population which comprises freezing and thawing the GRP cell population.

In one embodiment, the GRP cell population is manufactured in accordance with the present invention and further frozen and thawed after harvesting.

As will be understood by the skilled artisan upon reading this disclosure, however, alternative methods for manufacturing the GRPs prior to freezing can be used. For example, in one embodiment, the GRP cell population is manufactured by a method wherein A2B5-positive cells are cultured for 6 DIV or less. The cultured cells are then harvested and frozen. After thawing, the cells can be cultured for 3 or more additional days in vitro (DIV) to increase cell number.

Further, immunophenotyping with this selected panel of antibodies provides a useful reliable means to characterize this cellular therapeutic. Thus, another aspect of the present invention relates to this antibody panel for characterizing GRP cells comprising A2B5, GFAP, and one or more antibodies selected from the group consisting of Olig1, Olig2, O1, PDGFR-α, nestin, NG2, PSA-NCAM, TuJ1, Ki-67 and NeuN and methods for characterizing cells as GRP cells and/or documenting the purity of the cell population with this panel of antibodies. In one embodiment, cells are characterized using the antibody panel by first plating the cells according to standard protocols on coverslips or in multichamber slides or the like, allowed to grow overnight under standard tissue culture conditions, and then fixed and stained according to standard procedures. Immunopositive cells are identified using standard microscopy methods, and the percentages of cells positive for each antibody are defined relative to the total number of cells (as defined by a pan nuclei stain: DAPI or the like). The following immunophenotype using this antibody panel is indicative of a population of mammalian cells being GRPs: a majority of cells are positive for A2B5 and one or more of GFAP, nestin, NG2, PDGFR-α, Olig1, Olig2 and O1 and a majority of cells are negative for one or more of PSA-NCAM, TUJ1, PECAM, CD68, and NeuN. By "majority" as used herein it is meant that greater than 50% of the cells are positive or negative for the selected antibody.

In addition to immunocytochemical characterization of the cellular product, gene targets whose expression correlates with the different types of cells that may be found in the cell isolates have been identified. Gene expression data were collected from unpurified cells, GRP cells harvested at 6-DIV originating from 15 brain tissues and GRP cells produced in accordance with the method of the present invention. Approximately 375 genes showed at least 5-fold changes in expression level (increasing and decreasing levels) with a P value of ≤0.01 between GRP cells harvested at 6-DIV and unpurified cells. Using these data, gene expression profiles may be generated and evaluated via techniques such as chip/array analysis, multiplex RT-PCR and qPCR as a means for identifying cell populations.

Also provided in the present invention is a method for manufacturing mammalian neural cells depleted of A2B5-positive cells. In this method, A2B5 antibody-reactive cells are isolated from a mammalian tissue source capable of generating A2B5 positive cells. Cells that remain after removing the A2B5 antibody-reactive cells are then collected. In one embodiment of this method, the cells are cultured for one or more days in vitro (DIV) on a substrate. In this method, the collected cells may optionally be further depleted of certain cell types by freezing and thawing the cell population.

Another aspect of the present invention relates to method for generating astrocytes and/or oligodendrocytes from the GRPs manufactured in accordance with the present invention. In this method, the GRP cells manufactured in accordance with the present invention are cultured under conditions which promote differentiation to astrocytes and/or oligodendrocytes. In one embodiment, the GRP cells are cultured under conditions which promote differentiation to astrocytes. Two nonlimiting examples of media formulations that promote astrocyte differentiation include: 1) growth of GRPs in DMEM/F12, N1 or N2 supplement, basic FGF, BMP4 with these growth factors present in the ng/mL range or the 10-100 ng/mL range; and 2) DMEM/F12, N1 or N2 supplement, 1-10% FBS, and basic FGF in the ng/mL range or the 10-100 ng/mL range. In another embodiment, the GRP cells are cultured under conditions which promote differentiation to oligodendroctyes. Two nonlimiting examples of media formulations and conditions that promote oligodendrocyte differentiation include: 1) growth of GRPs in DMEM/F12 medium lacking growth factors for two days, and transfer of cells to a DMEM/F12 medium supplemented with N2, PDGF-AA present in the ng/mL range or the 10-100 ng/mL range, and T3 in the 1-100 nM range; and 2) growth of GRPs in DMEM/F12 medium supplemented with N2, T3 in the 100's of nM range, N-acetyl cysteine in the tens of µg/mL range, and PDGF-AA and CNTF in the ng/mL range or the 10-100 ng/mL range.

Experiments were performed confirming that GRPs prepared in accordance with the method of the present invention exhibit defined and reproducible expression parameters of selected antigens, and are consistent in their ability to differentiate into astrocytes and oligodendrocytes, but not neurons, in an in vivo setting as well. Further, experiments showed that these GRPs exhibited characteristics of cell survival, migration and differentiation into myelin-producing oligodendrocytes as well as astrocytes in animal models. Together, these studies demonstrate that GRPs manufactured in accordance with the method of the present invention, successfully integrate, differentiate into oligodendrocytes and astrocytes, and remyelinate axons in demyelinated neural tissue of the brain and spinal cord.

Thus, the present invention also relates to methods for using GRP cells manufactured in accordance with the present invention to produce astrocytes and oligodendrocytes in vivo in mammals and to increase re-myelination of neurons in a mammal suffering from a disease, disorder, injury or damage associated with demyelination of neurons. Between 0.01 and 100 million cells can be administered by direct parenchymal transplantation using catheters or needles familiar to neurosurgeons skilled in the art, involving one or more injections. These transplantations can be performed after accessing the neural tissue directly by the use of a burr hole or laminectomy. Alternatively, the transplants can be performed into the spinal cord by CT-guided percutaneous delivery without the need for direct visual access of the neural target tissue by an interventional radiologist skilled in the art. Additionally, cells can be administered to the cerebrospinal fluid (CSF) such as via lumbar puncture or other suitable methods rather than directly into the parenchyma. Cells can also be administered by intravenous administration for certain diseases. Finally, several clinical trials with other neural cell types are currently being conducted for these diseases. Similar protocols and procedures used in these clinical trials with other neural cells can be adapted routinely by those of skill in the art for use with the GRPs manufactured in accordance with the present invention.

Survival, migration, proliferation, and differentiation of human GRPs manufactured in accordance with the present invention, when xenografted in the brains of the shiverer mouse, a model for glial behavior in vivo (Nave, J. Neurosci. Res. 1994 38:607-612), was demonstrated. The shiverer mouse possesses an autosomal recessive mutation that results in the failure of these mice to develop myelin basic protein (MBP). Endogenous oligodendrocytes formed in the CNS of shiverer mice fail to assemble compacted myelin (Privat et al., Neurosci. Lett. 1979 12:107-112). To maximize graft survival, a shiverer mouse strain that also carries an autosomal recessive mutation in the Rag2 gene which encodes a protein essential to the generation of mature B and T lymphocytes and therefore displays cell-mediated immune deficiencies was developed (Shinkai et al. Cell 1992 68:855-867). Newborn double-homozygous shiverer/rag2 immunodeficient mice were implanted with 100,000 human GRPs at a single site targeting the subventricular zone. Eight or 12 weeks after implantation animals were sacrificed and the survival and distribution of human GRPs and their progeny was assessed immunocytochemically. The widespread distribution of human cells documents the ability of the human GRPs to survive and migrate in this genetically immune compromised model. Similar results of the in vivo survival, migration and differentiation in shiverer/rag2 have been observed with both 6 DIV and 20 DIV GRPs.

The differentiation potential of human GRPs in vivo was assessed immunocytochemically in brain sections from these mice. One group of mice was sacrificed at eight weeks post-implantation while another group was sacrificed for humane reasons at a time when neurological deterioration resulted in markedly impaired ambulation and frequent episodes of sustained seizures (typically 12- to 18-weeks postnatal). Brain sections were stained with anti-myelin basic protein (MBP; expression of intact MBP recognized by this antibody is not observed in shiverer mice, thus, expression of MBP is solely from implanted human GRPs) and anti-human GFAP antibodies (which does not recognize murine GFAP). While quantification of astrocyte and oligodendrocyte numbers was not feasible, it was confirmed that the two cell types were generated from human GRPs in vivo by measuring the area of MBP and GFAP immunoreactivity in vivo post sacrifice. These data detail the ability of human GRPs of the present invention to differentiate into the appropriate cell phenotypes.

Dual staining of the brain sections using antibodies against NeuN, a protein expressed in most neurons, and human nuclear antigen (HuNA) was also carried out. These data were collected from the same animals used to determine MBP and GFAP expression. Human GRPs in an animal sacrificed at eight weeks were concentrated near the corpus callosum and less than 0.3% HuNA/NeuN double positive cells were observed. The ability of these cells to differentiate into glia and not neurons is relevant to use in neurodegenerative diseases, wherein aberrant axonal sprouting associated with allodynia-like hypersensitivity when neural stem cells (which give rise to both neurons and glia) have been used as a cellular therapy has been reported (Hofstetter et al. Nat. Neurosci. 2005 8:346-353; Macias et al., Exp. Neurol. 2006 201:335-348).

Cell survival and distribution of human GRPS was also assessed following intraspinal cord administration in rats. Sixty-thousand (60,000) human GRPs in a volume of 1-μL were implanted into the spinal cords of 12 athymic rats at the level of C-4. Four animals were sacrificed at each of three time points (1, 4, and 12 weeks post-implant). Animals were perfused with paraformaldehyde at sacrifice, their spinal cords harvested, and 1-cm of cervical cord was analyzed for the presence of human GRPS using HuNA antibody staining of transverse sections. No proliferating masses were detected in the spinal cords of athymic rats implanted with human cells after one, four, and 12 weeks post-implantation. Survival of implanted human cells was observed at the four and 12 week time points. Human GRPs were present throughout the cross-sectional area of the spinal cord, with the greatest cell density observed in the dorsal column where the injections were performed. One out of four animals at one week post-implantation and four out of four animals at 4 and 12 weeks post-implantation had human GRPs present upon necropsy. At four weeks, approximately ⅔ of the sections analyzed had human GRPs (rostro-caudal spread of 0.63-cm); and at 12 weeks all of the sections analyzed had human GRPs (rostro-caudal spread of 1-cm).

Cell survival and distribution of human GRPs prepared in accordance with the process of the present invention following intraspinal cord administration with two different cell dosages was determined. No spinal cord abnormalities were detected by gross necropsy at 28 days post-implantation. Immunocytochemical analysis using HuNA and Ki-67 antibodies revealed no proliferating masses in the spinal cords of athymic rats at either dose of 800,000 or 1,200,000 total human GRPs/animal. Human GRPs were present throughout the cross-sectional area of the spinal cord, with the greatest cell density observed in the dorsal column where the injections were performed. Co-localization of HuNA/Ki-67 was very low in the animals injected with 800,000 total cells and human GRPs were detected in all sections stained with HuNA antibody over the entire 1-cm spinal cord segment that was analyzed. Human GRP cell density in the spinal cord of rats injected with 1,200,000 total cells was too high to manually count; however, a visual assessment of HuNA/Ki-67 co-localization was similar to that observed in the low dosage animals.

Conditions have been established to induce a focal inflammatory demyelinated lesion on the spinal cord of Lewis rats. This animal model mimics the pathology of Transverse Myelitis in humans and was used to define the ability of transplanted human GRPs produced in accordance with the present invention to survive in the vicinity of the induced focal demyelinated lesion. The rat model is based on a published model (Kerschensteiner et al., Am. J. Pathol. 2004 164:1455-1469) that has been modified to more reliably induce clinical and histologic evidence of focal inflammatory demyelination. Adult Lewis rats were immunized with myelin oligodendrocyte glycoprotein (MOG) suspended in incomplete Freund's adjuvant followed 10 days later by a T9 laminectomy and injection of a cocktail of Tumor Necrosis Factor α, Interleukin 6, Interferon α, and ethidium bromide (EtBr). Focal inflammation in the dorsal column of a Lewis rat was observed four days after injection of the cocktail. Active inflammation was largely resolved 10-14 days after injection of the cytokines and EtBr; however, extensive demyelination of the region persisted. Human GRPs implanted into this region were detected at 3, 8, and 14 weeks after implantation with a rostro-caudal spread of up to 13 mm, demonstrating that they can survive in demyelinated lesions.

Survival of human GRPs produced in accordance with the present invention in an inflammatory environment mimicking that of multiple sclerosis was also assessed. Dark Agouti female rats (150-175 grams body weight) were injected with 10-mg of MOG in incomplete Freud's adjuvant at the base of the tail. Rats developed clinical disease (EAE score of 2.5-3.0; hind-limb paresis) at 10-12 days post-immunization. Starting two days prior to human GRP cell implantation, and daily thereafter, rats were injected with cyclosporine A at 10-mg/kg IP. Laminectomies were performed at the thoracic level (T8-T9) and each animal received a single injection of approximately 150,000 human GRPs in 2-μL of saline into the dorsal column. Animals were implanted with human GRPs at two or seven days post-disease symptoms. Animals were sacrificed at one week, two weeks, and four weeks post-implantation. Engrafted human GRP cells were detected using HuNA antibody in 40-μm transverse sections of spinal cord near the implant site. OX42 antibody was used to detect CD11b on the surface of host activated microglia which are present during an inflammatory response. Hematoxylin and eosin (H&E) staining was used to determine macrophage and microglia infiltration. HuNA staining closely localized to immunostaining with OX42 one week post-transplantation. Pronounced H&E staining around the injection site is also indicative of host infiltration of macrophage and microglia. By two weeks post-transplantation, HuNA co-localization with OX42 immunostaining was no longer observed, while H&E staining was still observed, although less pronounced. Transplanted human GRPs were able to survive in the DA/EAE rat spinal cord up to twelve weeks, the longest time point assessed, following injection at both two days and seven days post-disease initiation. Thus, human GRPs are able to survive under conditions that mimic those found in inflammatory lesions of human multiple sclerosis.

The demonstrated efficacy herein of the GRP cells manufactured in accordance with the present invention in multiple animal models for glial cell-related neurodegenerative diseases or disorders is indicative of their utility in treating or alleviating symptoms of these neurodegenerative diseases or disorders. Glial cells have been shown to play important roles in the pathogenesis of the neurodegenerative disease Amyotrophic Lateral Sclerosis (ALS) (Howland et al. PNAS 99, 1105, 1995; Clement et al. Science 302, 113, 2003; Rothstein et al. Ann. Neurol. 38, 73, 1995). Astrocytes play many important functions in the CNS, including cerebrovascular regulation, modulation of synaptic transmission (e.g. glutamate transport) as well as other effects including release of growth factors and provision of trophic support for neurons as well as glia. Glial cells may also reduce or prevent formation of reactive astrocytes, which cause deleterious effects in many neurodegenerative diseases, and glial cells may reduce levels of glial scarring such as occurs in spinal cord injury and several neurodegenerative diseases. Furthermore, transplantation of normal glial cells, which subsequently differentiated into astrocytes, into a rat model of ALS has been demonstrated to be neuroprotective in this model (Lepore et al. Nature Med. 11, 1294, 2008). These data indicate the therapeutic benefit of glial progenitors in a model neurodegenerative disease, and further studies indicate that glial progenitor cell therapy will be of benefit in other neurodegenerative diseases or disorders including but not limited to Parkinson's, Alzheimer's, Huntington's, and Alexander diseases (Maragakis and Rothstein Nature Clinical Practice Neurology 2, 679, 2006), multiple sclerosis (Windrem et. al. Cell Stem Cell. 2008 Jun. 5; 2(6):553-65, Hardison et. al Exp Neurol. 2006 February; 197(2):420-9), other demyelinating diseases (Duncan, J Inherit Metab Dis. 2005; 28(3):357-68) and spinal cord injury (Keirstead et. al. J. Neurosci. 2005 May 11; 25(19):4694-705, Mitsui et. al. J. Neurosci. 2005 Oct. 19; 25(42):9624-36.

Accordingly, another aspect of the present invention relates to methods for use of mammalian GRP cells manufactured in accordance with the present invention in the treatment of glial cell related neurodegenerative diseases or disorders in mammals as well as injuries or damage to the nervous system or a portion thereof. By injury or damage it is meant to include damage or injury induced by any cause including, but not limited to, trauma, drugs, radiation, and immune-mediated damage or injury. Additionally, it is expected that by supplying healthy glial cells which produce associated growth factors, etc., cells of the present invention will be useful in treating neurodegenerative diseases or disorders as well as injuries to the nervous system in mammals not specifically glial cell related. In these treatment methods, between one and 100 million cells manufactured in accordance with the present invention can be administered by direct parenchymal transplantation using catheters or needles familiar to neurosurgeons skilled in the art. These transplantations can be performed after accessing the neural tissue directly by the use of a burr hole or laminectomy. Alternatively, the transplants can be performed into the spinal cord by CT-guided percutaneous deliver without the need for direct visual access of the neural target tissue by an interventional radiologist skilled in the art. Additionally, cells can be administered to the CSF via lumbar puncture rather than directly into the parenchyma. Finally, several clinical trials with other neural cell types are currently being conducted for these diseases. Similar protocols and procedures used in these clinical trials with other neural cells can be adapted routinely by those of skill in the art for use with the GRPs manufactured in accordance with the present invention.

What is claimed is:

1. A method for manufacturing mammalian glial restricted progenitor (GRP) cells, said method comprising:
    (a) isolating A2B5 reactive cells by single antibody selection for A2B5-positive cells from a mammalian tissue source capable of generating A2B5 positive cells;
    (b) culturing the A2B5-positive cells for greater than 6 days in vitro (Div) on a substrate having a surface treated for adherence of cells;
    (c) harvesting the cultured cells; and
    (d) freezing the cultured cells after harvesting and then thawing to reduce unintended cellular phenotypes PSA-NCAM and TuJ1 while maintaining A2B5, GFAP and Ki-67 positive phenotypes,
    wherein said manufactured mammalian GRP cells exhibit tightened variability and decreased unintended cellular phenotypes as compared to cells harvested at 6 DIV and as compared to cells not frozen and thawed; or
    wherein said manufactured mammalian GRP cells exhibit increased growth and plating efficiency as compared to cells cultured in suspension.

2. The method of claim 1 wherein A2B5 reactive cells are isolated using magnetic activated cell sorting.

3. The method of claim 2 wherein cells are passed two or more times over a column comprising magnetic beads to isolate A2B5 reactive cells.

4. The method of claim 1 wherein A2B5 reactive cells are isolated using fluorescence activated cell sorting or immunopanning.

5. The method of claim 4 wherein cells are passed two or more times over a fluorescence activated cell sorting or immunopanning dish.

6. The method of claim 1 wherein the cells are cultured for 10-20-DIV.

7. The method of claim 1 wherein the cells are cultured for 15-20 DIV.

8. The method of claim 1 wherein the cells are cultured for at least 20 DIV.

9. The method of claim 1 wherein the cells are cultured for 100 DIV or greater.

10. A method for manufacturing mammalian glial restricted progenitor (GRP) cells, said method comprising:
  (a) dissociating mammalian neural tissue into a cell suspension;
  (b) isolating A2B5 reactive cells by single antibody selection for A2B5-positive cells;
  (c) culturing the A2B5-positive cells for greater than 6 days in vitro (DIV) on a substrate having a surface treated for adherence of cells;
  (d) harvesting the cultured cells; and
  (e) freezing the cultured cells after harvesting and then thawing to reduce unintended cellular phenotypes PSA-NCAM and TuJ1 while maintaining A2B5, GFAP and Ki-67 positive phenotypes,
  wherein said manufactured mammalian GRP cells exhibit tightened variability and decreased unintended cellular phenotypes as compared to cells harvested at 6 DIV and as compared to cells not frozen and thawed; or
  wherein said manufactured mammalian GRP cells exhibit increased growth and plating efficiency as compared to cells cultured in suspension.

11. The method of claim 10 wherein the mammalian neural tissue is obtained from a mammal after neural tube closure.

12. The method of claim 10 wherein the mammalian neural tissue is fetal cadaver forebrain tissue, fetal cadaver spinal cord tissue or mammalian biopsy brain or spinal cord tissue.

13. The method of claim 10 wherein the mammal is a human and the neural tissue is fetal cadaver forebrain tissue from gestational weeks 14 through 24.

14. The method of claim 10 wherein dissociating neural tissue is performed enzymatically.

15. The method of claim 10 wherein dissociating neural tissue is performed mechanically.

16. The method of claim 10 wherein dissociating neural tissue is performed mechanically and enzymatically.

17. The method of claim 10 wherein A2B5 reactive cells are isolated using magnetic activated cell sorting.

18. The method of claim 17 wherein cells are passed two or more times over a column comprising magnetic beads to isolate A2B5 reactive cells.

19. The method of claim 10 wherein A2B5 reactive cells are isolated using fluorescence activated cell sorting or immunopanning.

20. The method of claim 19 wherein cells are passed two or more times over a fluorescence activated cell sorting or immunopanning dish.

21. The method of claim 10 wherein the cells are cultured for 15-20 DIV.

22. The method of claim 10 wherein the cells are cultured for at least 20 DIV.

23. The method of claim 10 wherein the cells are cultured for 100 DIV or greater.

24. A method for generating astrocyte precursor cells, astrocytes, oligodendrocyte precursor cells and/or oligodendrocytes comprising culturing GRP cells manufactured in accordance with the method of claim 1 under conditions which promote differentiation to astrocyte precursor cells, astrocytes, oligodendrocyte precursor cells and/or oligodendrocytes.

25. The method of claim 24 wherein the GRP cells are cultured under conditions which promote differentiation to astrocyte precursor cells and/or astrocytes.

26. The method of claim 24 wherein the GRP cells are cultured under conditions which promote differentiation to oligodendrocyte precursor cells and/or oligodendroctyes.

27. The method of claim 24 wherein the GRP are cultured under conditions which promote differentiation to astrocytes and/or astrocyte precursor cells and oligodendrocyte precursor cells and/or oligodendrocytes.

28. A method for generating astrocytes and oligodendrocytes in a mammal, said method comprising administering to the mammal mammalian GRP cells manufactured in accordance with the method of claim 1.

29. A method for increasing re-myelination of neurons in a mammal suffering from a disease, disorder, injury or damage associated with demyelination of neurons, said method comprising administering to the mammal mammalian GRP cells manufactured in accordance with the method of claim 1.

30. A method for treating a neurodegenerative disease or disorder or injury or damage to the nervous system or a portion thereof in a mammal, said method comprising administering to the mammal mammalian GRP cells manufactured in accordance with the method of claim 1.

31. The method of claim 1 wherein the substrate having a surface treated for adherence of cells comprises poly-L-ornithine, poly-L-lysine or one or more recombinant or natural extracellular matrix molecules or fragments thereof selected from laminin, fibronectin or a xeno-free substrate for attachment and expansion of human embryonic, mesenchymal, and neural stem cells.

32. The method of claim 10 wherein the substrate having a surface treated for adherence of cells comprises poly-L-ornithine, poly-L-lysine or one or more recombinant or natural extracellular matrix molecules or fragments thereof selected from laminin, fibronectin or a xeno-free substrate for attachment and expansion of human embryonic, mesenchymal, and neural stem cells.

* * * * *